United States Patent
Wu et al.

(10) Patent No.: US 9,193,660 B2
(45) Date of Patent: Nov. 24, 2015

(54) PROCESS FOR RECOVERY OF A CARBOXYLIC ACID FROM A FEED STREAM CONTAINING THE CORRESPONDING ESTER

(71) Applicants: Kuang-Yeu Wu, Plano, TX (US); Pai-Yu Polly Chiang, Dallas, TX (US); Ji-Young Jang, McKinney, TX (US); Karl Tze-Tang Chuang, Edmonton, CA (US)

(72) Inventors: Kuang-Yeu Wu, Plano, TX (US); Pai-Yu Polly Chiang, Dallas, TX (US); Ji-Young Jang, McKinney, TX (US); Karl Tze-Tang Chuang, Edmonton, CA (US)

(73) Assignee: AMT International Inc., Plano, TX (US)

( * ) Notice: Subject to any disclaimer, the term of this patent is extended or adjusted under 35 U.S.C. 154(b) by 209 days.

(21) Appl. No.: 13/986,969

(22) Filed: Jun. 20, 2013

(65) Prior Publication Data
US 2014/0378703 A1    Dec. 25, 2014

(51) Int. Cl.
*C07C 51/42* (2006.01)
*B01D 3/00* (2006.01)
*C07C 51/09* (2006.01)
*C07C 51/44* (2006.01)

(52) U.S. Cl.
CPC .................. *C07C 51/42* (2013.01); *B01D 3/009* (2013.01); *C07C 51/09* (2013.01); *C07C 51/44* (2013.01)

(58) Field of Classification Search
CPC ............................. C07C 51/44; C07C 51/487
See application file for complete search history.

(56) References Cited

U.S. PATENT DOCUMENTS 6,518,465 B2 * 2/2003 Hoyme et al. ................ 568/698

OTHER PUBLICATIONS

Xiao et al, Chemical Engineering Science, Increase MeOAc conversion in PVA production by Replacing the Fixed Bed Reactor with a Catalytic Distillation Column, 2001, 56, pp. 6553-6562.*

* cited by examiner

*Primary Examiner* — Paul A Zucker
(74) *Attorney, Agent, or Firm* — George A. Seaby (57) ABSTRACT

A carboxylic acid e.g. acetic acid, is recovered from an aqueous feed stream containing the corresponding ester, an alcohol and a small amount of water by catalytically dehydrating the alcohol to the corresponding ether and water, and reacting the water with the ester to generate a liquid carboxylic acid rich product stream. The acid is recovered by distillation. In a second embodiment, additional alcohol and/or water are cofed with the feed or fed directly to a catalytic distillation column, resulting in a liquid bottom product stream of substantially pure acetic acid and a top distillate stream of substantially pure ether.

4 Claims, 4 Drawing Sheets

PROCESS FOR RECOVERY OF A CARBOXYLIC ACID FROM A FEED STREAM CONTAINING THE CORRESPONDING ESTER

CROSS-REFERENCE TO RELATED APPLICATIONS

This application is a divisional of application Ser. No. 12/737,767 filed Aug. 11, 2009.

FIELD OF THE INVENTION

The present invention relates to recovery of a carboxylic acid from an aqueous feed stream containing the corresponding ester and alcohol, and in particular to recovery of acetic acid from an aqueous feed stream containing methyl acetate and methanol, from a polyvinyl alcohol production process.

BACKGROUND OF THE INVENTION

Several industrial processes produce streams containing one or more esters of carboxylic acids, RO.CO.R', where R and R' are selected from among hydrocarbyl radicals or substituted hydrocarbyl radicals. Examples of such industrial processes include those for production of vinyl alcohol polymers or terephthalic acid. Carboxylic acid esters can be hydrolyzed to generate the corresponding acid and alcohol, as shown in Equation 1. Equation 1 is an equilibrium reaction and requires an excess of water to drive the reaction well to the right hand side.

$$RO.CO.R' + H_2O \rightleftharpoons ROH + HO.CO.R'' \quad [1]$$

Processes for production of polyvinyl alcohol (PVA) and its derivatives are described by Marten in "Vinyl Alcohol Polymers" in Kirk-Othmer Encyclopedia of Technology, John Wiley & Sons, Inc. A variety of vinyl ester monomers can be polymerized to form a polymer, of which polyvinyl acetate (PVAc) is preferred. PVAc then is further reacted to manufacture PVA. Commonly, PVAc is reacted with methanol (MeOH) to form PVA and methyl acetate (MeOAc). The components of the polymerization reaction mixture are continuously separated. Unreacted monomer can be stripped from the reactor using, for example, methanol vapor. The overhead fraction from the stripper comprises a mixture of vinyl ester monomer and at least one solvent such as methanol. The vinyl ester monomer is then extracted for recycle to the polymerization reactor. In the production of polyvinyl alcohol (PVA) MeOAc is produced as a by-product at a ratio of 1.68 tons of MeOAc per ton of PVA.

One outlet stream typically comprises a mixture including MeOAc, MeOH and a small amount of water. The weight ratio of these components varies over a range of relative concentrations, among which a typical composition is approximately 75% MeOAc, 23% MeOH and 2% water. Among these components MeOH and water have relatively low value when compared to the values of MeOAc and acetic acid (HOAc).

The MeOH and MeOAc can be distilled off and, at the same time, water can be added in order to obtain an aqueous PVA solution. However, there are disadvantages to this approach. The resulting PVA suspension is fine, difficult to filter, and so the process is uneconomical. Further, this approach requires time-consuming, energy intensive and hence expensive distillation of large amounts of solvents requiring a plurality of distillation columns. Several approaches have been undertaken to improve the chemical efficiency and economics of processes for production of PVA. In particular, efforts have been directed to recycle of solvents and processing of the outlet streams to recover valuable by-products.

Kowaka et al. in U.S. Pat. No. 6,743,859 issued in 2004 describe a method for production of high-strength PVA with a high degree of saponification. The apparatus for the process of '859 includes an outlet line for recovery of MeOH and MeOAc identified in FIGS. 1 through 3 by the reference numeral 7, however no details are presented for the process for the separation and recovery of those components.

Bauer et al. in U.S. Pat. No. 6,576,720 issued in 2003 describe an alternative approach in which a liquid phase comprising MeOH, MeOAc and HOAc is recycled for use in further polyvinyl ester transesterification. The process of '720 can be used for other alcohols and esters. The mixture of alcohol and corresponding ester is recycled for use as the polymerization reaction medium. Make-up comprising one or both of MeOH and HOAc is provided to maintain the composition of the recycle mixture. The PVA is produced and isolated using saponification with KOH and then neutralization, preferably with a strong acid such as HCl. Thus water, less than 1% by weight in the initial reaction mixture, is produced by both the reaction of MeOH and HOAc and the neutralization process.

MeOAc may be sold or further hydrolysed to recover HOAc.

Kim et al. in U.S. Pat. No. 5,770,770 issued in 1998 describe a reactive distillation process for the well known equilibrium reaction 2 for the recovery of MeOH and HOAc from catalytic hydrolysis of MeOAc. Reaction 2 is a specific example of the type of reaction shown in Equation 1.

$$MeOAc + H_2O \rightleftharpoons MeOH + HOAc \quad [2]$$

It has long been recognized that this reaction could be used to recover HOAc from MeOAc from a PVA manufacturing process as described, by example, by Adelman et al. in U.S. Pat. No. 4,352,940 issued in 1982. It also was recognized in '940 that it was necessary to minimize the amount of water used in the process to reduce the costs of recovery and re-use of the products from the reaction in the PVA manufacture process. However, when a minimum amount of water is used, the equilibrium reaction 2 lies to the left hand side. Reaction 2 can be driven to the right hand side only by continuous removal of at least one of the products.

In an alternative approach for treatment of the PVA manufacture outlet stream, MeOAc can be separated from the mixture using extractive distillation. One example of this method is described by Xiao et al. in Chemical Engineering Science, volume 56, pages 6553-6562 (2001). In the first column, water is added to the liquid stream from the PVA plant. The volatiles from the first column are then hydrolyzed in a fixed bed reactor containing a bed of an acidic catalyst which catalyzes the hydrolysis of MeOAc to MeOH and HOAc. The effluent stream from the fixed bed reactor is distilled in a second distillation column to provide a volatiles stream and a bottoms stream. The volatiles from the second column are recycled for mixing with further MeOAc feed to the first extractive distillation column. The bottoms from the second column are separated into a water rich stream and a HOAc rich stream by distillation in a third column. The bottoms from the first column are separated by distillation in a fourth column into a water rich stream and a MeOH rich stream. Thus the overall process for recovery of HOAc requires four distillation columns and a fixed bed reactor. Further, to drive well to the right hand side the well known catalytic MeOAc hydrolysis equilibrium reaction shown as Equation 2, it is necessary to use a large amount of water.

Thus the process is energy intensive as that water must be volatilized in both the second and third columns.

Each of the above processes requires use of a plurality of columns and reactors to react, separate and recover the components of the stream from the PVA manufacturing reactor. Consequently, capital and operating costs are high. Further, when water is added, either as reagent or for extractive distillation, that water must also be separated, which is a costly and time consuming feature.

Hoyme et al. in U.S. Pat. No. 6,518,465 issued in 2003 describe another concept based process, derived from simulations using the commercial available program Aspen Plus, in which the stream containing MeOAc from PVA manufacture is reacted in a reactive distillation column to produce DME and HOAc. Water was added to hydrolyze MeOAc and thereby generate HOAc which is recovered. The molar ratio of water in the process stream is between 0.05% and 20%, and preferably is between 0.3% and 3%. In this process it is recognized that methanol also may react to generate dimethyl ether (DME) and water in the also well known acid catalyzed equilibrium reaction shown in Equation 3. The process of Hoyme et al. in '465 is basically hydrolysis of MeOAc to HOAc by addition of water.

[3]

$$2MeOH \rightleftharpoons Me_2O + H_2O \quad [3]$$

SUMMARY OF THE INVENTION

It is an object of the present invention to provide an apparatus and process for separation and recovery of a carboxylic acid e.g. acetic acid (HOAc) produced by hydrolysis of the corresponding ester, in the exemplary case methyl acetate (MeOAc), in an aqueous feed stream containing the ester and alcohol e.g. methyl alcohol, from a reactor in which polyvinyl alcohol (PVA) is produced.

According to a first embodiment of the invention, an apparatus is provided for recovery of a carboxylic acid e.g. HOAc, from an aqueous feed stream containing the corresponding ester e.g. MeOAc and alcohol e.g. MeOH and a small amount of water, and in some cases the acid e.g. HOAc, by catalytic distillation of the aqueous stream to form a carboxylic acid e.g. HOAC and the corresponding ether e.g. DME, the apparatus comprising a catalytic distillation column containing an acidic catalyst and a distillation column for carboxylic acid e.g. HOAc recovery as a liquid bottoms product stream.

In a second embodiment of the apparatus, means is provided for addition of a supplemental amount of methanol and/or water, either to the feed stream before it is fed into the catalytic distillation column, or directly into the column at an appropriate location on the column, to maintain optimum operation of the process independent of the composition of the ester containing feed stream from which the carboxylic acid e.g. acetic acid, is to be recovered, to provide a volatile tops product stream that is substantially pure DME, and a liquid bottoms product stream that is substantially pure acetic acid. In this case, there is no need for a distillation column to separate acetic acid from the liquid bottoms product stream.

According to another aspect of the first embodiment of the present invention a process is provided for recovery of a carboxylic acid e.g. HOAc, from an aqueous feed stream containing the corresponding ester e.g. MeOAc and alcohol e.g. MeOH and a small amount of water and in some cases the acid e.g. HOAc, comprising
(a) supplying the aqueous feed stream to a catalytic distillation column containing an acidic catalyst, wherein, in one reaction the alcohol is dehydrated to produce the corresponding ether and water, and in another reaction this water is used to hydrolyze the ester to the corresponding alcohol and acid, wherein both reactions proceed concurrently in reversible equilibrium, to produce a bottoms liquid product stream containing the acid exiting the catalytic distillation column, and
(b) transferring the bottoms product stream to a distillation column from which substantially pure acid is recovered as a liquid bottoms product stream.

According to the process aspect of the second embodiment of the invention, a supplemental amount of methanol and/or water is added, either to the feed stream before it is fed into the catalytic distillation column, or directly into the column at an appropriate location on the column, to maintain optimum operation of the process independent of the composition of the ester containing feed stream from which the carboxylic acid e.g. acetic acid, is to be recovered, to provide a volatile tops product stream that is substantially pure DME, and a liquid bottoms product stream that is substantially pure acetic acid.

By way of further explanation, in the process according to the invention, in the catalytic distillation column, reactive distillation in the presence of an acidic catalyst, is used for conversion of an aqueous feed stream containing MeOAc-MeOH and a small amount of water, and in some cases HOAc, respectively to HOAc and DME, through a two-step concurrent reaction process. One reaction involves the reversible equilibrium dehydration of MeOH to form DME and water. The other reaction employs this water to react with MeOAc in the reversible equilibrium hydrolysis reaction that produces MeOH and HOAc. The MeOH produced during hydrolysis of MeOAc is then able to participate further in MeOH dehydration to produce more water. In effect, the two reactions are "self-feeding" and can be visually represented as follows:

$$MeOH \rightleftharpoons DME + H_2O \quad H_2O + MeOAc \rightleftharpoons HOAc + MeOH$$

A significant benefit of the reactive distillation process of the first embodiment of the invention is that no additional water is added as feed and the process continues as long as there is water and/or MeOH in the column to react. Once the MeOAc-MeOH azeotrope has been broken, any further separation of MeOAc and HOAc in a liquid bottoms product stream becomes a matter of simple distillation.

A significant benefit of the second embodiment is that a distillation column is not required to separate the HOAc.

BRIEF DESCRIPTION OF THE DRAWINGS

For a more complete understanding of the present invention and for further description of objects and advantages thereof, reference is made to the following accompanying drawings in which.

DETAILED DESCRIPTION OF THE INVENTION

The following description comprises data obtained through laboratory experiments and simulations using ASPEN PLUS® software. However, in order to perform the simulations and thereby correlate experimental data with theory, it was necessary to obtain data on the physical and chemical equilibria occurring in the respective reaction mixtures. The data for individual reactions 2 and 3 are available in the open literature. However, no physical and chemical kinetic data were available for mixtures comprising all five components involved. To obtain accurate simulation results, experiments were performed to obtain kinetic data for reactions among combinations of all five components. The following brief descriptions provide background data available and the measures taken to determine the equilibria parameters.

As a consequence of having experimental data on physical and chemical equilibria that were hitherto unavailable to those skilled in the art, the construction, experimental demonstration and modeling of the process comprising the invention described herein have higher reliability than those described elsewhere. For the first time, we show accurately a process comprising the two concurrent continuous reversible equilibrium reactions occurring in a single reactor, one generating water and DME from MeOH and another consuming said water by reaction with MeOAc to generate both MeOH and HOAc. Water generated in one reaction is consumed in the other, and MeOH generated in the latter reaction is consumed in the former.

We are for the first time able to compute fully the roles and impacts of each of the components in the reaction mixture, experimentally verify the computed data, and so establish operating parameters so that in the first embodiment of the invention:

there is essentially no water generated in the overall process, and substantially all water is consumed when there is excess MeOAc to undergo hydrolysis;

DME is recovered as a substantially pure volatile distillate in the overhead;

a liquid bottoms stream that is rich in HOAc is generated in the catalytic distillation column for transfer to a distillation column for recovery of essentially anhydrous substantially pure HOAc, separately from recovery of DME; and the process has high overall energy efficiency, as there is no requirement for consumption of energy to remove added high concentrations of water.

Accordingly, the process of the present invention offers advantages over those described in the prior art.

We will now show that in the first embodiment of the invention, components of the liquid bottoms product stream from a single catalytic distillation column reactor in which the two reversible equilibrium reactions are occurring, include a much higher concentration of HOAc than the feed stream, along with MeOAc and smaller amounts of additional components. For the overall process to operate with high energy efficiency and generate substantially pure HOAc, it is necessary that the liquid bottoms from the catalytic distillation column are transferred to a separate simple distillation column.

In the second embodiment of the invention, using either a batch reactor or a continuous reaction system, if the feed composition is adjusted through addition of a supplemental amount of methanol and/or water, either to the feed stream or to the catalytic distillation column, substantially pure HOAc can be produced in a single catalytic distillation column because DME is very volatile and can be completely removed from the feed stream reaction mixture. Accordingly, it is a feature of the second embodiment of the invention that all methyl species are converted when DME is completely removed as a distillate in a tops product stream by catalytic distillation, with the consequence that the liquid bottoms stream is substantially pure HOAc. In this case, a distillation column is not required.

Physical Equilibria:

An important consideration in any reactive distillation simulation is the choice of physical equilibrium model and the ability to reliably predict multicomponent vapour-liquid equilibria (VLE) and liquid-liquid equilibria (LLE). Reliable VLE and LLE are needed to establish distillation boundaries and to determine if and where azeotropes and phase separations occur. There exists an abundance of patchwork/piecemeal phase equilibrium data in the open literature on the multicomponent mixture of MeOAc-MeOH-water-HOAc-DME and the respective subsystems. The various equations used to model these systems take into account the non-ideality of the vapor phase (due to dimerization of HOAc).

Chemical Equilibria:

The two concurrent reversible reactions considered in the process are the hydrolysis of MeOAc and the dehydration of MeOH. The hydrolysis of MeOAc with water over an acid catalyst produces HOAc and MeOH (Equation 2). Reaction 2 is equilibrium limited with a reported equilibrium constant of 0.13 at 25° C. (Ge et al., "Kinetics of Heterogeneous Hydrolysis of Methyl Acetate", Chemical Reaction and Engineering and Technology (Chinese Journal), Vol. 14, No. 2, 1998, pp 138-144). The dehydration of methanol, consumes two moles of methanol to produce one mole of DME and one mole of water (Equation 3).

The equilibrium constant has been reported to range from 68.4 to 52.3 in the temperature range from 85° C. to 115° C. (Nisoli et al., "Attainable Regions for Reaction with Separation" in AIChE Journal, Vol. 43, No. 3 (2), 1997, pp 374-387). The overall reaction is given by:

MeOAc+MeOH ⇌ DME+HOAc [4]

Because water is both consumed and produced stoichiometrically, it drops out of the overall reaction equation.

The Invention:

An exemplary embodiment of the invention, which is non-limiting, will now be described with reference to FIG. 1 through FIG. 5. By way of example, the apparatus and process parameters described for the first embodiment will be presented with reference to recovery of HOAc by hydrolysis of MeOAc from a feed stream mixture fed to the apparatus from a PVA manufacturing facility. The feed stream (mixture) typically includes MeOAc, MeOH and water, although it could also contain some HOAc. If and when some HOAc is included in the feed stream, some impact in the equilibrium reactions described above would occur. It is noted that the spec of feed streams at PVC plants does not include HOAc. However, since HOAc is used extensively at these plants, it is therefore possible that some streams may be contaminated with HOAc.

It will be recognized that the method and the principles of operation of the apparatus will apply to recovery of other lower carboxylic acids from other mixtures, when the operating parameters are amended according to the properties of those carboxylic acids and the esters from which they are recovered.

Figure 1:
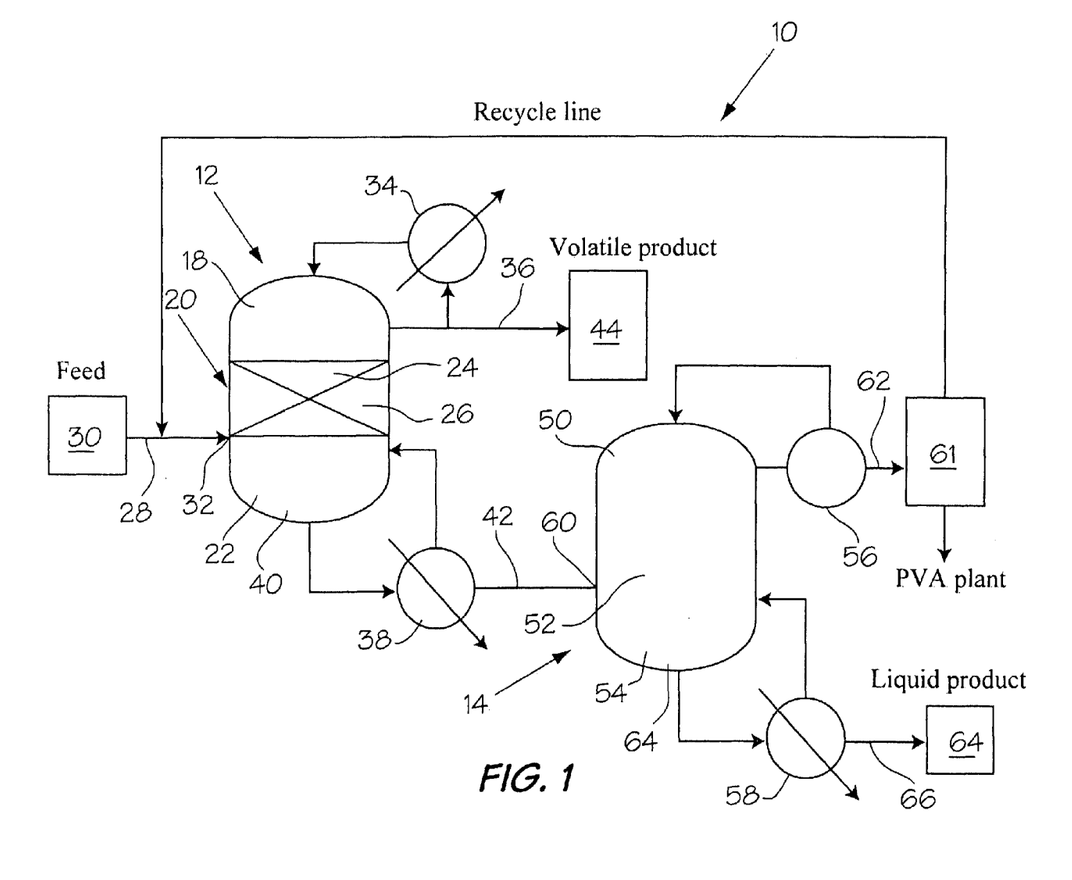
FIG. 1 is a schematic diagram of the apparatus according to the invention including a catalytic distillation column and a distillation column.

Referring to FIG. 1, an apparatus 10 includes a catalytic distillation column 12 and a distillation column 14. The term "catalytic distillation" as used herein refers to the concurrent reversible equilibrium chemical reactions of the components within a feed stream mixture, at least one reaction occurring in the column being catalyzed by a catalyst.

Catalytic distillation column 12 has a top portion ("rectifying zone") 18, a middle portion ("reactive zone") 20 and a bottom portion ("stripping zone") 22. A fixed bed 24 containing an acidic catalyst 26 is situated within middle portion 20 of catalytic distillation column 12.

When, for example, a feed 30 is an MeOAc rich stream from a chemicals manufacturing facility (not illustrated) such as a PVA manufacturing facility, a feed line 28 carries feed 30 to a location 32 on the catalytic distillation column, closely below fixed bed 24. A first condenser 34 is used to condense a portion of vapors in top portion 18, from which a fraction is recycled to distillation column 12 and another fraction is recovered as first volatiles product 44 via a first volatiles outlet line 36. A first reboiler 38 is used to reboil a portion of first liquid bottoms 40 exiting bottom portion 22 for recycle to catalytic distillation column 12, and another portion of first liquid bottoms 40 is removed via a first liquid bottoms outlet line 42.

Acidic catalyst 26 can be one or more of several different acidic catalysts. It has been found through experiments that any one of several acidic resin catalysts is suitable for use in the catalytic hydration of MeOAc according to Equation 2, including but not limited to use of the acidic forms of commercially available resins, Amberlyst® 15, 35 or 37. Amberlyst® catalysts are widely used for acid catalyzed reactions. They contain $SO_3H+$ reactive sites attached to a styrene divinyl benzene copolymer.

Distillation column 14 has a top portion 50, a middle portion 52, a bottom portion 54, a second condenser 56 and a second reboiler 58. The another portion of first liquid bottoms 40 from catalytic distillation column 12 is fed via first liquid bottoms outlet line 42 to a position 60 approximately midway up middle portion 52 of distillation column 14. The optimum position 60 for connection of first liquid bottoms outlet line 42 and distillation column 14 has been determined experimentally using modeling and predicted operating performance data have been confirmed experimentally, as described in the EXAMPLES below.

Second condenser 56 condenses a portion of vapors in top portion 50 for recycle to distillation column 14, and another portion is recovered as a second volatiles product 61 via a second volatiles outlet line 62. Second reboiler 58 reboils a portion of a second liquid bottoms 64 in bottom portion 54 of distillation column 14, and another portion of second liquid bottoms 64 is recovered via a second liquid bottoms outlet line 66.

When the chemicals processing facility manufactures one or more of PVA and derivatives of PVA, feed 30 is a stream from the manufacturing facility typically comprising MeOAc, MeOH and water. It is desirable to recover acetic acid, which may be recycled for use in manufacture of vinyl acetate which in turn can be polymerized for manufacture of PVA. The ether formed from dehydration of MeOH is DME and it is recovered as first volatiles product 44. DME can be recovered for sale or for other use.

The second volatiles product 61 from distillation column 14 is much richer in MeOAc than was feed 30, and this stream can be recovered for sale or recycled to distillation column 12.

Figure 3:
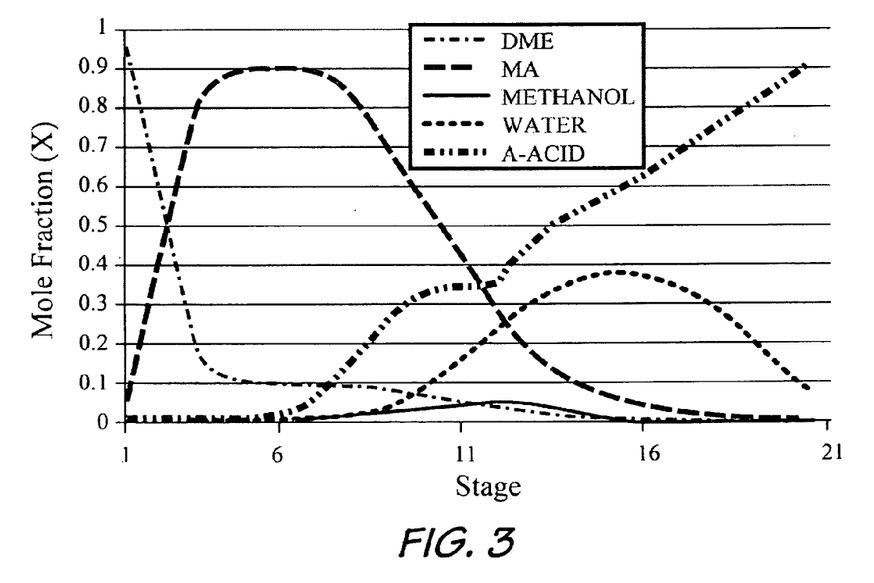
FIG. 3 is a graph showing the effect of excess water on product distribution in the CD column.
Figure 4:
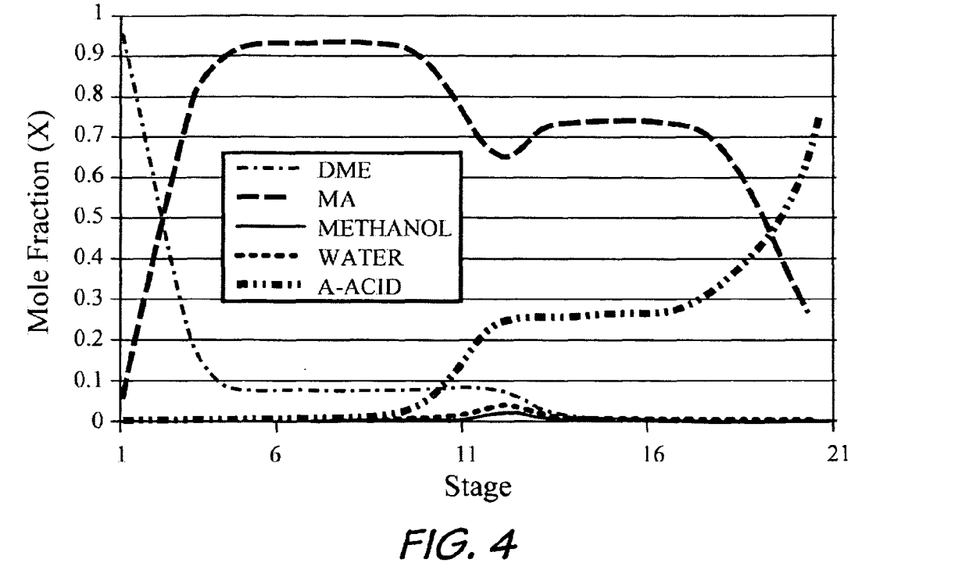
FIG. 4 is a graph showing the effect on product distribution in the CD column when there is no water content in the feed.
Figure 5:
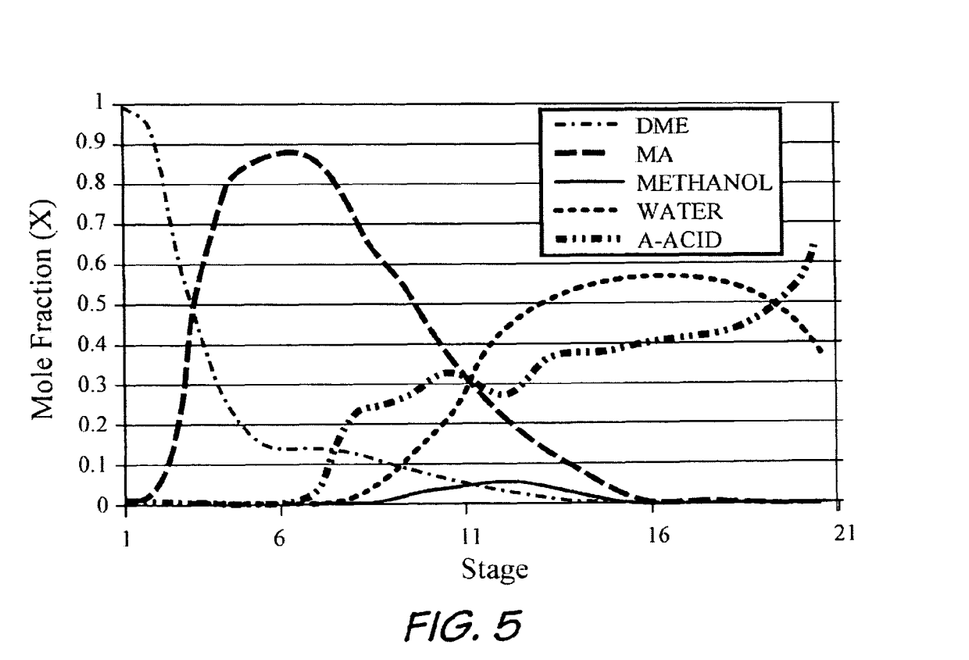
FIG. 5 is a graph showing the effect on the composition profile when the MeOAc-MeOH feed is in molar ratio 0.55; RR=1.8, D/F=0.475, T=120° C. and P=150 psi.

The method of use of apparatus 10 will now be illustrated with reference to FIGS. 3 through 5, using as the example reaction hydrolysis of MeOAc for recovery of HOAc.

The composition of feed 30 from a PVA manufacturing facility is shown in Table 3. Also in Table 3 are the compositions, for one exemplary set of operating parameters, of that portion of first volatile products 44 recovered via first volatiles outlet line 36 and that portion of first liquid bottoms 40 removed via first liquid bottoms outlet line 42.

Laboratory experiments, described in EXAMPLE 1 below, showed that the rate of dehydration of MeOH to form DME (Equation 3) is affected by the concentrations of both water and MeOH in the aqueous feed stream mixture 30 initially comprising MeOH-water-HOAc-MeOAc. Thus, to maintain efficient operation, it is desirable that the mixture fed to catalytic distillation column 12 has an optimum composition profile.

The second embodiment of the present invention enables more efficient operation of the process independent of variations that may occur from time to time in the composition of feed 30 before it is fed via feed line 28 into catalytic distillation column 12, illustrated in FIG. 1. At least one additional feed line (not illustrated) is provided that independently can feed additional amounts of one or both of methanol and water to catalytic distillation column 12. Depending on the composition of feed 30, additional methanol and/or water may be added into feed line 28 before feed 30 or at appropriate locations on catalytic distillation column 12. We found that the consequence of ensuring a substantially optimum concentration profile of both methanol and water along the catalytic distillation column 12 is that the operation of the process occurring therein is production of substantially pure DME and HOAc, without the need for a distillation column, so the operating cost for the process is minimized.

A benefit from use of the second embodiment of the present invention is that the apparatus is more versatile. The capability to provide a supplemental amount of one or both of methanol and water in addition to feed 30 can be used for recovery of substantially pure HOAc from a variety of different industrial streams containing the corresponding hydrolysable ester.

Another benefit arising from use of apparatus 10 for the second embodiment of the present invention is that the process can be operated so as to produce a stream of substantially pure DME and HOAc as products. In this embodiment, DME is continuously removed as a volatile tops stream from apparatus 10 so that substantially all methyl species are converted to DME and are thus removed from the system, with the consequence that first liquid bottoms 40 comprises substantially pure HOAc.

The following EXAMPLES will illustrate applications of the apparatus and method for recovery of HOAc according to the invention. Each set of conditions has been modeled using ASPEN® software and results from modeling have been confirmed through experiment.

EXAMPLES

Example 1

Batch Distillation

Figure 6:
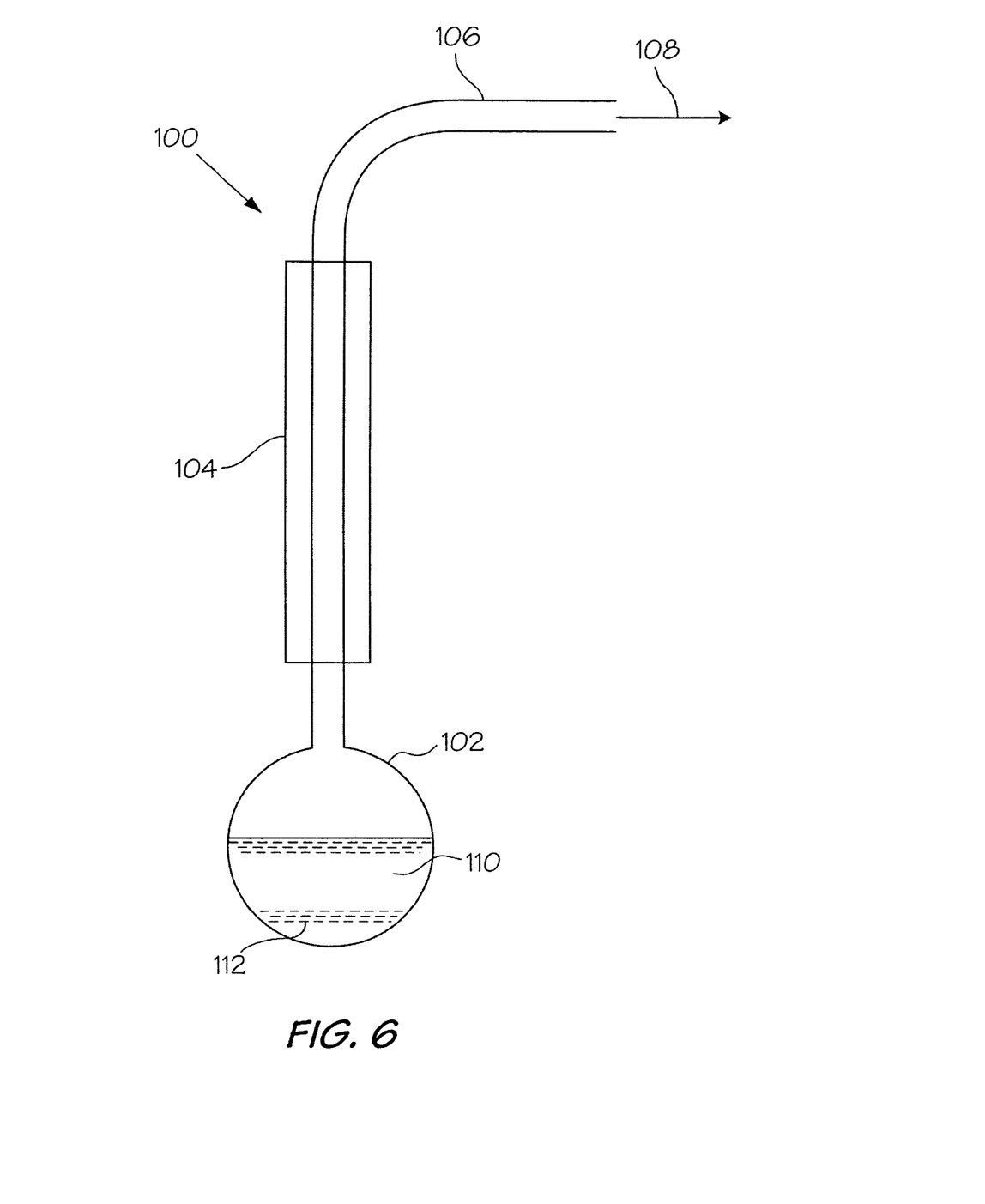
FIG. 6 is a schematic diagram showing the apparatus according to the invention for experiments to determine the effect of mixture composition on production of DME.

Laboratory experiments were conducted to confirm literature data and to obtain additional insights into the two catalytic reactions for the formation of DME and HOAc, using an apparatus 100 illustrated in FIG. 6. Apparatus 100 for conducting batch non-equilibrium experimental reactions comprised a reaction vessel 102, a condenser 104 and a line 106 for recovery and analysis of a DME containing stream 108. The feed 110 comprised several different mixtures of MeOH, water and MeOAc in different ratios. Each reaction mixture 110 and catalyst 112 were mixed in reaction vessel 102 and refluxed. The amount of the DME containing stream 108 exiting via line 106 was determined gravimetrically and its composition was determined using gas chromatography. Using apparatus 100 it was found that the rate of DME and HOAc formation depended upon the composition of reaction mixture 110 as well as the concentration of catalyst 112 therein. In particular, it was found that the formation of DME depended on the amounts of water and MeOH present in reaction mixture 110. The data so obtained were then used to design and simulation of the process.

Using the system demonstrated in these laboratory experiments and illustrated in FIG. 6, that all methyl groups from MeOAc can be removed as DME, thus producing a liquid product rich in HOAc, which remains in the reaction vessel 102. In this further embodiment of the process, sufficient MeOH and/or water are added to reaction mixture 110 so as to hydrolytically cleave all methyl groups from MeOAc. The methyl groups are removed as DME by volatilization. The products formed are a liquid product rich in HOAc and a volatile distillate product rich in DME. In this case, a distillation column is not needed to recover acetic acid.

Example 2

Model Batch Catalytic Distillation

To examine the reliability and effectiveness of the physical and reaction equilibrium models, a batch catalytic distillation simulation was performed and compared to experimental data collected in the lab.

For the experimental test, a batch Parr reactor was loaded with a 150 g mixture of MeOAc/MeOH feed in a 75:25 weight ratio, along with 30 g of previously dried acid catalyst (Amberlyst 35®). The top of the batch reactor was modified with a stainless steel condenser, which allowed the most volatile component (i.e., DME) to escape. The condenser was cooled with cold water; GC analysis of the off-gas from the condenser confirmed that >99% DME was leaving the reactor. The reactor was operated at 120° C. and 150 psig over a period of 13 hours until equilibrium had been reached. It was determined that equilibrium was established based on vapor and liquid samples from the reactor which showed constant concentration over several samples. Vapor and liquid samples were measured on an HP® 6890 GC equipped with capillary column and TCD. A two-stage equilibrium reactor with distillation, column was sufficient to model the batch distillation process in Aspen Plus®. Table 1 shows the liquid composition for the batch catalytic distillation simulation and compares it to experimental batch catalytic distillation results.

TABLE 1

Liquid product composition for batch catalytic
distillation experiment and simulation at T = 120° C.
and P = 150 psi for MeOAc/MeOH mass feed ratio of 75:25.

| Component | Simulation "Product" stream Weight % | Experimental Product stream Weight % |
|---|---|---|
| MeOAc | 58.5 | 69.25 |
| MeOH | 2.1 | 2.87 |
| DME | 9.8 | 3.5 |
| Water | 4.0 | 3.31 |
| HOAc | 25.7 | 21.06 |

Comparison of data from the simulation and experimental results confirms that the predictions from our model are accurate in terms of reaction rate and equilibrium constants.

Example 3

Simulation of Continuous Catalytic Distillation Column

The continuous catalytic distillation process consists of a 20 stage CD column with total condenser and partial reboiler. The parameters for the base case simulation are given in Table 2. All feed streams enter at 25° C.

TABLE 2

Parameter values for the base case used in Aspen Plus ® simulations

| Parameter | Value |
|---|---|
| Column pressure (atm) | 5 |
| Distillate to feed ratio (D/F) | 0.45 |
| Reflux ratio (RR) | 2.1 |
| Total number of stages | 20 |
| Reaction stage location | 3 to 16 (inclusive) |
| Feed stage location (above stage) | 12 |
| Feed composition (mass basis): | |
| MeOAc | 0.75 |
| MeOH | 0.23 |
| H$_2$O | 0.02 |

Example 4

Effect of Pressure

Figure 2:
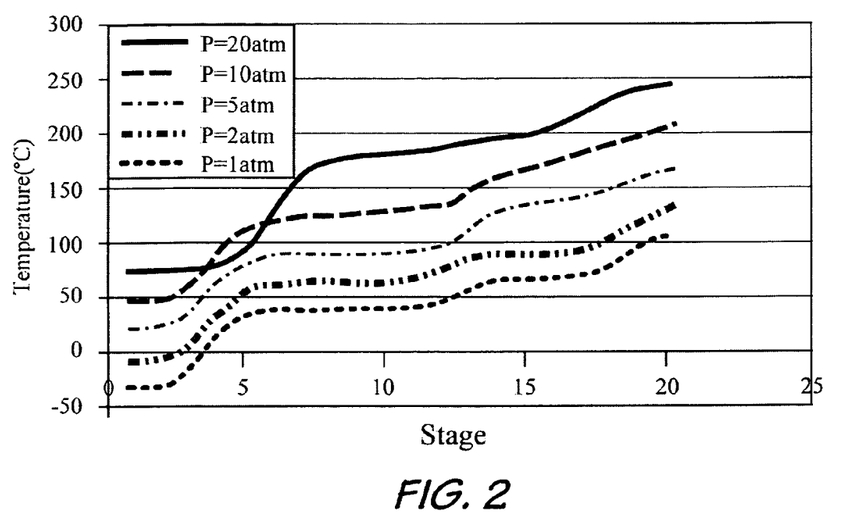
FIG. 2 is a graph showing the effect of changing pressure on the temperature profile in the catalytic distillation column.

Operating pressure is one of the key elements in the design of a CD column. The choice of operating pressure for a catalytic distillation column depends on many considerations such as the overhead temperature, bottom temperature, reaction temperature and relative volatilities of the components in the system. The column pressure sets the lower and upper bounds of the temperature within the column. For the present process the operating pressure is chosen within a range such that water can be used as a coolant for the overhead condenser and steam can be used as a heating medium for the reboiler. Within this range, the reaction temperature mainly determines the operating pressure. Because the catalytic reactions take place within the liquid phase, the reaction temperature is close to the boiling point of liquid flowing around the catalyst. As a result the reaction temperature increases with column pressure. FIG. 2 shows the effect of column pressure on the temperature profile in the column. In these simulations the parameters are those as in the base case, except for the reflux ratio. As column pressure was increased, the reflux ratio was also increased concurrently in order to achieve mathematical convergence in the simulation. The reflux ratio was increased by the minimum amount that would satisfy convergence of the CD column, with all other parameters being held constant.

Example 5

Effect of Water

The amount of water in the feed is an important variable in the CD process because water is a necessary reactant in the hydrolysis reaction. However, water is also produced via MeOH dehydration. Therefore, there should be an optimum amount of water that will allow both reactions to proceed readily without accumulating a large amount of water in the reaction mixture. The optimum process achieves maximum conversion of reactants while at the same time completely removing water from any of the product streams. FIG. 3 shows the effect of excess water content of the feed stream (relative ratio of MeOAc:MeOH in the feed remains constant). When excess water enters as a component of the feed the hydrolysis reaction is limited by the concentration of MeOAc. MeOAc is completely consumed and excess water exits with HOAc in the bottoms product.

Conversely, when no water enters in the feed, only the water that is produced through MeOH dehydration is available for the hydrolysis reaction. In this case DME is again the distillate product, and a mixture of HOAc and MeOAc is now the liquid bottoms product. All of the water and MeOH is reacted away. The resulting profile of concentrations of all CD column reaction mixture components is shown in FIG. 4.

Example 6

Effect of MeOAc/MeOH Ratio

Based on the overall reaction equation given by equation (4), one might predict that the there should be very little influence on the process arising from changes in the ratio of MeOAc to MeOH. Increasing either MeOH or MeOAc in the feed should favour DME and HOAc product formation. However, based on the stoichiometry of the individual reactions, this is not necessarily true. The effect of increasing the MeOAc/MeOH feed ratio results in complete conversion of water and methanol in the CD column with a profile similar to that shown in FIG. 4. When considering only the hydrolysis reaction, one would expect that by increasing the amount of MeOAc in the feed, water could be more easily reacted to completion. When water is consumed and MeOH is produced, the equilibrium for the dehydration consequently shifts to favor the production of DME. When the MeOAc/MeOH ratio decreases below a specific stoichiometric amount, the MeOAc reactant becomes the limiting reactant.

Simulation results show that column parameters can be varied to completely remove both MeOAc and MeOH from the column mixture, and a mixture of water and HOAc remains as the bottoms product. FIG. 5 illustrates this effect when using a MeOAc/MeOH molar feed ratio of 0.55.

Example 7

Simulation of the Process of the First Embodiment

Catalytic distillation column 12 has 20 stages. Feed 30 comprises a mixture containing about 75% MeOAc, 23% MeOH and 2% water, and is fed at 100 kg·h$^{-1}$ into stage 12 into catalytic distillation column 12 at 100° C. The pressure under which feed 30 is supplied is 10 atm. The column operates at 5 atm. and so feed 30 is supplied via a back-pressure regulator (not illustrated). The reflux ratio is 2 and the distillate-to-feed ratio is 0.45. At steady state, the temperature at stage 3, at the top of the reaction zone is 31° C. and at the bottom of the reaction zone, stage 16, is 127° C.

First volatile products 44 exiting top portion 18 of catalytic distillation column 12 comprises almost entirely DME (over 99%; Table 3). First liquid bottoms 40 exiting bottom portion 22 of catalytic distillation column 12 comprises about 91% HOAc and the balance is less than 9% MeOAc, with only trace amounts of MeOH, water and DME (Table 3).

More specifically, first volatiles product 44 comprises close to 100% DME. First liquid bottoms 40 comprises a mixture of about 91% HOAc, 8.9% MeOAc, 0.04% water, and traces of MeOH and DME.

Distillation column 14 has 10 stages and has a reflux ratio of 7 and a distillate-to-feed ratio of 0.07. First liquid bottoms 40 from catalytic distillation column 12 is fed at stage 5 into distillation column 14 at a temperature of 170.5° C. and a pressure of 5 atm.

Second liquid bottoms 64 from distillation column 14 is substantially pure HOAc (see Table 4). Second volatiles product 60 is rich in MeOAc and is recyclable.

TABLE 3

Composition of feed and product streams for catalytic distillation column 12 in Example 7.

| | Flow rates (kg · h$^{-1}$) | | |
|---|---|---|---|
| Component | Feed 30 | First volatiles product 44 | First liquid bottoms product 40 |
| MeOAc | 75 | 0.093 | 5.50 |
| MeOH | 23 | <0.001 | 0.0025 |
| HOAc | | <0.001 | 56.26 |
| Water | 2 | <0.001 | 0.026 |
| DME | | 3.81 | <0.001 |

TABLE 4

Composition of feed and product streams for distillation column 14 in Example 7.

| | Flow rates (kg·h$^{-1}$) | | |
|---|---|---|---|
| Component | Feed (first liquid bottoms product 40) | Second volatiles product 61 | Second liquid bottoms product 64 |
| MeOAc | 5.50 | 5.20 | 0.31 |
| MeOH | 0.0025 | <0.002 | <0.001 |
| HOAc | 56.26 | 0.025 | 56.24 |
| Water | 0.026 | 0.005 | 0.021 |
| DME | <0.001 | <0.001 | <0.001 |

REFERENCES CITED

U.S. Patent Documents

| | | | |
|---|---|---|---|
| 4,352,940 | October 1982 | Adelman et al. | 562/607 |
| 5,770,770 | June 1998 | Kim et al. | 562/608 |
| 6,518,465 | February 2003 | Hoyme et al. | 568/698 |
| 6,576,720 | June 2003 | Bauer et al. | 526/70 |
| 6,743,859 | June 2004 | Kowaka et al. | 525/62 |

OTHER REFERENCES

Ge, X., Wang, Z, Yong, J., Yang D., "Kinetics of Heterogeneous Hydrolysis of Methyl Acetate" Chemical Reaction and Engineering and Technology (Chinese Journal), Vol. 14, No. 2, 1998, pp 138-144.

Gmehling, J., Bölts, R., "Azeotropic Data for Binary and Ternary Systems at Moderate Pressures" Journal of Chemical Engineering Data, Vol. 41, No. 2, 1996, pp 202-209.

Marten, F. L., "Vinyl Alcohol Polymers" in Kirk-Othmer Encyclopedia of Chemical Technology, John Wiley & Sons, Inc.

Nisoli, A., Malone, M. F., Doherty, M. F., "Attainable Regions for Reaction with Separation" American Institute for Chemical Engineering Journal, Vol. 43, No. 3 (2), 1997, pp 374-387.

Teshima, T., Hiyoshi, S., Matsuda, H., Monma, S., and Iwaba, S., "Extractive distillation, II. Vapor-liquid equilibrium relation of methyl acetate-methanol-water system" Vol. 55, 1952, pp 801-803).

Xiao, J., Liu, J., Juntai, L., Jiang X., and Zhang, Z., "Increase in MeOAc conversion in PVA production by replacing the fixed bed reactor with a catalytic distillation column" Chemical Engineering Science, 56, 6553-6562 (2001).

The invention claimed is:

1. A process for the recovery of acetic acid from an aqueous feed stream containing methyl acetate, methyl alcohol and a small amount of water and in some cases acetic acid, comprising
   (a) supplying the aqueous feed stream to a catalytic distillation column containing an acidic catalyst, wherein in one reaction the alcohol is dehydrated to produce dimethyl ether and water, and in another reaction this water is used to hydrolyze the methyl acetate to methyl alcohol and acetic acid, wherein both reactions proceed concurrently in reversible equilibrium, and
   (b) adding a supplemental amount of methanol and/or water, either to the feed stream before it is fed into the catalytic distillation column, or directly into the column to maintain optimum operation of the process independent of the composition of the ester containing feed stream from which the acetic acid is to be recovered to provide a volatile tops product stream that is pure dimethyl ether, and a liquid bottoms product stream that is pure acetic acid.

2. A process according to claim 1, wherein the acidic catalyst is selected from the acidic forms of commercially available resins, containing $SO_3H+$ reactive sites attached to a styrene divinyl benzene copolymer.

3. A process according to claim 2, wherein the aqueous feed stream is a stream produced at a facility for manufacturing at least one product from among polyvinyl alcohol and derivatives of polyvinyl alcohol.

4. A process according to claim 1, wherein dimethyl ether is continuously removed from the system so that all methyl species in the feed stream are converted to dimethyl ether and thereby removed from the reaction mixture, and the liquid product stream is pure acetic acid.

* * * * *